(12) United States Patent
Takenouchi et al.

(10) Patent No.: US 6,287,819 B1
(45) Date of Patent: Sep. 11, 2001

(54) PROCESS FOR PRODUCING URIDINE DIPHOSPHATE-N-ACETYLGLUCOSAMINE

(75) Inventors: Kenji Takenouchi, Choshi; Kazuya Ishige, Hasakimachi; Yuichiro Midorikawa, Choshi; Kiyoshi Okuyama, Narutomachi; Tomoki Hamamoto; Toshitada Noguchi, both of Choshi, all of (JP)

(73) Assignee: Yamasa Corporation, Chiba (JP)

( * ) Notice: Subject to any disclaimer, the term of this patent is extended or adjusted under 35 U.S.C. 154(b) by 0 days.

(21) Appl. No.: 09/297,306

(22) PCT Filed: Aug. 11, 1998

(86) PCT No.: PCT/JP98/03561

§ 371 Date: Apr. 29, 1999

§ 102(e) Date: Apr. 29, 1999

(87) PCT Pub. No.: WO99/11810

PCT Pub. Date: Mar. 11, 1999

(30) Foreign Application Priority Data

Aug. 29, 1997 (JP) .................................................. 9-249461

(51) Int. Cl.[7] ........................................................ C12P 19/30
(52) U.S. Cl. ........................................................ 435/89
(58) Field of Search ................................................ 435/89

(56) References Cited

U.S. PATENT DOCUMENTS

| | | | |
|---|---|---|---|
| 4,569,909 | * | 2/1986 | Seno et al. .............................. 435/89 |
| 4,604,349 | * | 8/1986 | Seno et al. .............................. 435/11 |
| 5,674,715 | * | 10/1997 | Tomita et al. .......................... 435/89 |

FOREIGN PATENT DOCUMENTS

| | | |
|---|---|---|
| 49-8278 | 2/1974 | (JP) . |
| 8-23993 | 1/1996 | (JP) . |
| 10-28594 | 2/1998 | (JP) . |

OTHER PUBLICATIONS

Tatsurokuro Tochikura et al.; Agricultural and Biological Chemistry, vol. 35, pp. 163–176, 1971 XP000912295.

\* cited by examiner

*Primary Examiner*—Herbert J. Lilling
(74) *Attorney, Agent, or Firm*—Wenderoth, Lind & Ponack, L.L.P.

(57) ABSTRACT

A process for producing uridine diphosphate-N-acetylglucosamine (UDPAG) from uridylic acid (UMP) and N-acetylglucosamine by use of microorganism cells, characterized by adding N-acetylglucosamine kinase thereto. According to the present invention, UDPAG can be efficiently produced even when N-acetylglucosamine is used as a substrate.

10 Claims, 3 Drawing Sheets

PROCESS FOR PRODUCING URIDINE DIPHOSPHATE-N-ACETYLGLUCOSAMINE

This Application is a 371 of PCT/JP98/03561 filed Aug. 11, 1998.

DESCRIPTION

1. Technical Field

The present invention relates to a process for producing uridine diphosphate-N-acetylglucosamine (UDPAG), an important substrate in the synthesis of oligosaccharides.

2. Background Art

Recent remarkable progress in sugar chain science has clarified some of sugar's physiological roles, making possible the development of pharmaceuticals and functional materials based on oligosaccharides possessing physiological activities. However, currently only limited types of oligosaccharides are commercially available, and those which are commercially available are extremely expensive. Moreover, these oligosaccharides may be produced only on a reagent level, and a mass production method therefor has not necessarily been fully established.

Conventionally, oligosaccharides have been produced by extraction from natural substances, chemical synthesis, enzymatic synthesis, or a combination of these methods. Among these processes, enzymatic synthesis has been considered best suited for mass production, for the following reasons: (1) enzymatic synthesis does not require intricate procedures, such as protection and removal of protection, which are required for chemical synthesis, and thus can provide oligosaccharides of interest with ease; and (2) substrate specificity of an enzyme enables synthesis of oligosaccharides having highly structural specificity. In addition, recent advances in recombinant DNA technology have made possible economical mass production of various types of enzymes, also contributing to establishing the superiority of enzymatic synthesis over other processes.

Two processes for the synthesis of oligosaccharides through enzymatic synthesis are available: a process making use of the reverse reaction of hydrolase, and a process making use of glycosyltransferase. The former has an advantage in that it may employ inexpensive monosaccharides as the substrate, but, because it employs the reverse reaction to the hydrolysis reaction, it is not necessarily the beat process in terms of synthesis yield and application to oligosaccharides of complicated structure.

In contrast, the latter process makes use of glycosyltransferase and has an advantage over the former in terms of the synthesis yield and application to the synthesis of oligosaccharides of complicated structure. Moreover, due to recent progress in recombinant DNA techniques, mass-production of various types of glycosyltransferase has also contributed to realization of this process.

However, sugar nucleotides, which are sugar donors and used in a synthesis making use of glycosyltransferase are, with few exceptions, still expensive, and are provided only in small amounts on reagent levels. For example, although there has been reported a process for preparing uridine diphosphate-N-acetylglucosamine (UDPAG)—which is a donor of N-acetylglucosamine contained in the core portion of any of a variety of physiologically active sugar chains—through a method which makes use of an osmolarity-resistant yeast (Japanese Patent Application Laid-Open (kokai) No. 8-23993), studies are required before realization of industrial production thereof.

The present inventors have conducted extensive studies on the biosynthesis route of UDPAG, and considered that the synthesis rate is determined by the acetylation reaction of glucosamine-6 phosphate to N-acetylglucosamine-6-phosphate, which occurs in a series of reactions starting from glucosamine to glucosamine-6 phosphate then to N-acetylglucosamine-6 phosphate and finally to N-acetylglucosamine-1 phosphate. If this is the case, use of N-acetylglucosamine-6 phosphate as a substrate may improve the yield in synthesis of UDPAG. However, at present, a large quantity of this substance is not available at a low price.

Consequently, it was presumed that if N-acetylglucosamine, which is currently available in large quantities at a low cost, is used as a substrate, the aforementioned rate-determining step may be eliminated, and N-acetylglucosamine may serve as a better substrate than glucosamine. Thus, the present inventors examined the UDPAG production process proposed by Tochikura at al. (Japanese Patent Publication (kokoku) No. 49-8278, Tochikura Process), in which UDPAG is produced with yeast cells from uridylic acid (UMP) and N-acetylglucosamine serving as substrates. However, their studies ended up with confirmation of the finding by Tochikura et al. that use of N-acetylglucosamine as a substrate resulted in lower, or even nil or very little, yield of UDPAG as compared with the case when glucosamine is used as a substrate.

Accordingly, the present invention is directed to a process for producing UDPAG at high yield, even in the case when N-acetylglucosamrine is used as a substrate.

DISCLOSURE OF THE INVENTION

The inventors of the present invention have carried out careful studies to achieve the aforementioned objectives, and found that (1) yeast cells have no or very little enzymatic activity for phosphorylation of N-acetylglucosamine, so that N-acetylglucosamine may not be a candidate substrate; however, if N-acetylglucosamine kinase, which is a phosphokinase for N-acetylglucosamine, is added to the reaction, UDPAG may be synthesized efficiently; (2) furthermore, addition of N-acetylglucosamine phosphate mutase and/or uridine diphosphate-N-acetylglucosamine pyrophosphorylase improves the yield of UDPAG, as compared with the case which makes use of N-acetylglucosamine kinase alone; and (3) UDPAC is synthesized efficiently from uridine triphosphate (UTP) by addition of N-acetylglucosamine kinase, N-acetylglucosamine phosphate mutase, and uridine diphosphate-N-acetylglucosamine pyrophosphorylase; thus completing the invention.

Accordingly, the present invention provides a process of producing UDPAG from UMP and N-acetylglucosamine by use of microorganism cells, which process is characterized by the addition of N-acetylglucosamine kinase in the process.

Further, the present invention provides a process of producing UDPAG from UTP and N-acetylglucosamine by use of enzyme, which process is characterized by combined use of N-acetylglucosamine kinase, N-acetylglucosamine phosphate mutase, and uridine diphosphate-N-acetylglucosamine pyrophosphorylase as enzymes.

BRIEF DESCRIPTION OF THE DRAWINGS

In FIG. 5, the figures enclosed in circles indicate the results when the following enzymes were added to the reaction mixture;

(1) yeast and N-acetylglucosamine kinase;
(2) yeast, N-acetylglucosamine kinase, and N-acetylglucosamine phosphate mutase;
(3) yeast, N-acetylglucosamine kinase, and UDPAG pyrophosphorylase;
(4) yeast, N-acetylglucosamine kinase, N-acetylglucosamine phosphate mutase, and UDPAG pyrophosphorylase.

Figure 6:
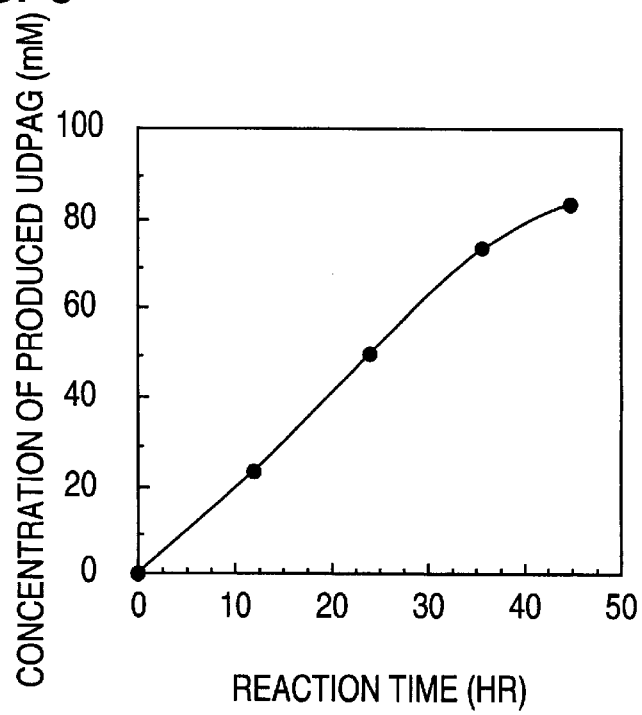

FIG. 6 is a graph showing chronological changes in the quantity of UDPAG produced in the co-presence of recombinant N-acetylglucosamine kinase derived from *Bacillus subtilis* M168, recombinant N-acetylglucosamine phosphate mutase derived from baker's yeast, and/or recombinant UDPAG pyrophosphorylase derived from *Escherichia coli* E102.

BEST MODE FOR CARRYING OUT THE INVENTION

As described above, the present invention relates to a process of producing UDPAG from UMP and N-acetylglucosamine by use of microorganism cells, which process is characterized by the addition of N-acetylglucosamrnne kinase In the process.

The microorganism cells used for the reaction in the present invention are not particularly limited so long as they may be employed for the production of sugar nucleotldes. For example, yeast cells, such as Saccharomyces, Zygosaccharomyces, Candida, Torulopsis, Hansenula, and Debaryomyces, may be used. Both viable and dry yeast cells may be used; however, dry yeast cells are preferred from the viewpoints of reaction yield and convenience in handling.

N-acetylglucosamine kinase derived from any source; e.g., animal, plant, or microorganism, may be added to the reaction. Among them, N-acetylglucosamine from microorganisms is preferred in view of convenience of enzyme preparation.

N-acetylglucosamine kinase is found ubiquitously in many types of microorganisms, such as Candida (Biochemica et Biophysica Acta, 614, 350(1980)), Streptococcus (Methods in Enzymology, 9, 415 (1966)), Escherichia (Methods in Enzymology, 9, 421, (1966)), and Bacillus and Klebsiella, and can be easily prepared from cultured cells.

Alternatively, N-acetylglucosamine kinase may be prepared through so-called recombinant DNA techniques; i.e., by cloning N-acetylglucosamine kinase gene according to a conventional method and inducing expression of the enzyme abundantly in microorganism cells.

N-acetylglucosamine kinase added to the reaction may assume any form so long as its activity is retained. For example, any of the following is acceptable: the enzyme as contained in microorganism cells, or in treated microorganism cells, or an enzymatic preparation prepared from the treated microorganism cells.

The microorganism cells may be prepared by culturing in a medium that permits their growth according to a routine method and collection by, for example, centrifugation. For example, for *Bacillus stearothermophilus* or *Klebsiella planticola*, there may be used bouillon medium, LB medium (1% tryptone, 0.5% yeast extract, 1% sodium chloride), or 2×YT medium (1.6% tryptone, 1% yeast extract, 0.5% sodium chloride). In these media, cells are inoculated and incubated at about 30–50° C. for about 10–50 hours with optional stirring according to need, and microorganism cells are collected by centrifugation of the culture liquid, to thereby obtain microorganism cells having N-acetylglucosamine kinase activity.

Examples of the treated microorganism cells may be in the form of lysate, or denatured cell walls or membranes obtained by various types of customary treatments, including mechanical destruction (by use of a Waring blender, French press, homogenizer, mortar, etc.); freezing/thawing; autolysis; drying (freeze drying, air drying, etc.); enzymatic treatment (by use of lysozyme, etc.); ultrasonic treatment; and chemical treatment (acid or alkali treatment, etc).

Examples of enzyme preparations include crude or purified enzymes recovered from fractions having enzymatic activity that are prepared from the aforementioned treated microorganism cells, by a conventional purification procedure for enzymes (such as salting-out, isoelectric precipitation, organic solvent precipitation, dialysis, or various types of chromatography).

The method for preparing N-acetylglucosamine kinase from microorganism cells is specifically described as follows: collection of microorganism cells, ultrasonic destruction, centrifugation, separation of supernatant, addition of ammonium sulfate into the supernatant, and precipitation in 30–54% saturated fraction. After the recovered precipitate is desalted, any type of chromatography, such as ion exchange chromatography or gel filtration, is performed, so as to concentrate and desalt N-acetylglucosamine-kinase-active fractions, to thereby obtain the target enzyme preparation.

Preferably, N-acetylglucosamine kinase is added to the reaction mixture at a concentration of about 0.001 unit/ml or more, particularly preferably within the concentration range of about 0.001 to about 100 unit/ml.

In the present invention, any commercially available UMP and N-acetylglucosamine may be used for the reaction. The concentration levels of these chemicals is not particularly limited; however, preferably any level within the range of about 1–200 mM, particularly preferably about 10–100 mM, may be applied.

In the present invention, inorganic phosphate and an energy source are preferably added to the reaction system. Potassium phosphate may be used as the Inorganic phosphate; however, phosphate buffer is more preferred. The pH of phosphate buffer is suitably chosen within the range of about 6.0–9.0. The concentration range is not strictly limited; however concentration is preferably about 10–500 mM, with about 100–300 mM being particularly preferred. As the energy source there may be used sugars such as glucose or fructose; or organic acids such as acetic acid or citric acid.

In the present invention, in combination with addition of N-acetylglucosamine kinase, addition of N-acetylglucosamine phosphate mutase and/or uridine diphosphate-N-acetylglucosamine pyrophosphorylase can improve the yield of UDPAG.

The species of N-acetylglucosamine phosphate mutase or uridine diphosphate-N-acetylglucosamine pyrophosphorylase which are caused to be co-present in the reaction system are not particularly limited, and may be selected among those derived from animals, plants, or microorganisms. Those derived from microorganisms are preferable in view of convenience of enzyme preparation. These enzymes may be prepared by recombinant DNA techniques; specifically, cloning of a gene of the enzyme and expression in a large quantity in microorganism cells.

Examples of microorganisms that can serve as sources for N-acetylglucosamine phosphate mutase include Saccharomyces (European Journal of Biochemistry, 221, 741 (1994)), Neurospora (Journal of Biological Chemistry, 219, 753 (1956)), Blastoclaudiella (Biochemica et Biophysica Acta 45, 408 (1976)), and yeast separated from commercially available baker's yeast.

Examples of microorganisms that can serve as sources for uridine diphosphate-N-acetylglucosamine pyrophosphorylase include Escherichia (Journal of Bacteriology 175, 6150 (1993)), Staphylococcus (Journal of Biological Chemistry, 234, 1822 (1959)), Saccharomyces (Agricultural Biological Chemistry, 40, 2275 (1976)), Neurospora (Can. J. Microbiology 25, 1381 (1979)), and *Escherichia coli*.

Like N-acetylglucosamine kinase, N-acetylglucosamine phosphate mutase and uridine diphosphate-N-acetylglucosamine pyrophosphorylase are found ubiquitously in many types of microorganisms, and therefore, they can easily be prepared from a microorganism cell culture.

N-acetylglucosamine phosphate mutase and uridine diphosphate-N-acetylglucosamine pyrophosphorylase, which are to be added to the reaction system, may assume any form so long as enzyme activity is retained. Examples include those present in microorganism cells, those present in treated microorganism cells, and enzyme preparations prepared from the treated microorganism cells. They may be prepared by the same methods as used for N-acetylglucosamine kinase.

The concentration of N-acetylglucosamine phosphate mutase and/or uridine diphosphate-N-acetylglucosamine pyrophosphorylase in the reaction mixture is preferably about 0.001 unit/ml or more, more preferably within the range of about 0.1–10 units/ml.

UDPAG may be produced, for example, by preparing a mixture of phosphate buffer, yeast, UMP, N-acetylglucosamine, and N-acetylglucosamine kinase, and, if needed, sugar serving as an energy source; and optionally adding thereto N-acetylglucosamine phosphate mutase and/or uridine diphosphate-N-acetylglucosamine pyrophosphorylase; to thereby perform a reaction at about 5–30° C., preferably about 5–25° C., for about 1–50 hours under stirring if desired.

UDPAG prepared by the above method may be isolated and purified by a conventional sugar nucleotide purification procedure, such as ion exchange chromatography, absorption chromatography, or salting-out.

A UDPAG production process from UTP and N-acetylglucosamine by use of N-acetylglucosamine kinase, N-acetylglucosaminephosphate mutase, and uridine diphosphate-N-acetylglucosamine pyrophosphorylase is described as follows.

N-acetylglucosamine kinase, N-acetylglucosamine phosphate mutase, and uridine diphosphate-N-acetylglucosamine pyrophosphorylase to be added to the reaction system may be the same as those used in the aforementioned process.

UTP and N-acetylglucosamine which are to be used in the reaction of the present invention may be any commercial species. The concentrations of these substrates may be selected within the range of approximately 1–200 mM, preferably 10–100 mM or thereabouts.

UDPAG synthesis may be performed, for example, by a procedure in which UTP and N-acetylglucosamine are added to buffer solution (pH about 6.0–9.0) and the three aforementioned enzymes are added in amounts of approximately 0.001 unit/ml or greater, preferably 0.001–100 units/ml or thereabouts, for causing a reaction. The reaction proceeds at about 5–30° C., preferably about 5–25° C., for 1–50 hours. If desired, the reaction mixture is stirred during reaction.

The thus-obtained UDPAG may be isolated and puritied by a conventional procedure employed for sugar nucleotides, as described previously.

In the present invention, a UTP-generating system may be used as a replacement for UTP in the UDPAG synthesis reaction system.

The UTP-generating system is not particularly limited so long as it can supply UTP to the reaction system, and there may be used any known method, such as a method making use of a microorganism or enzyme.

A specific example UTP-generating system employing microorganism is a UTP-generating system from arotic acid (e.g., Japanese Patent Application Laid-open (kokai) No. 5-276974). In one preferred method employing enzyme, the UTP-generating system and an ATP-regeneration system are coupled; i.e., adenylic acid (AMP) is treated with polyphosphate kinase, adenylate kinase, and polyphosphate to regenerate ATP and, simultaneously, UMP is treated with uridylate kinase and, if needed, nucleoside diphosphate kinase, to thereby generate UTP.

The conditions for a UDPAG synthesis reaction making use of a UTP-generating system are basically the same as those for the above-described UDPAG synthesis. Ultimate reaction conditions may be suitably selected by performing small-scale experiments for determining conditions which will allow a smooth synthesis reaction between UTP generation reaction and UDPAG synthesis reaction.

EXAMPLES

The present invention will next be described in detail by way of examples, which should not be construed as limiting the invention. In the Examples, UDPAG in a reaction mixture was quantified by HPLC; i.e., separation was performed by use of an ODS-AQ312 column (YMC Co.). Elution was performed with 0.5M potassium dihydrogenphosphate solution. Preparation of DNA, cleaving with restriction enzyme, ligation of DNA by use of T4 DNA ligase, and transformation of *Escherichia coli* were performed according to the method described in "Molecular Cloning" (Maniatis et al., Cold Spring Harbor Laboratory, Cold Spring Harbor, New York (1982)).

The restriction enzyme, AmpliTaq DNA polymerase, and T4 DNA ligase were purchased from Takara Shuzo K. K.

Example 1

(1) Preparation of N-Acetylglucosamine kinase

Cells of *Bacillus stearothermophilus* ATCC15952 in an amount of one platinum loop were inoculated in 10 ml of 2×YT medium (1.6% trypton, 1% yeast extract, 0.5% sodium chloride) and subjected to shaking culture at 50° C. for 24 hours. The resultant culture cells, i.e., pre-culture cells, were transferred into 100 ml 2×YT medium in a 500 ml flask, and subjected to shaking culture at 50° C. for 18 hours. The cells were collected by centrifugation from a 3-liter medium, and suspended into 500 ml 100 mM phosphate buffer (pH 7.0). After centrifugation of cell suspension, the collected calls were resuspended in 300 ml PEN (50 ml phosphate buffer (pH 7.6), 1 mM EDTA, 0.1 mM N-acetylglucosamine). The cells were ultrasonically lysed, and the supernatant obtained through centrifugation was separated as a crude enzyme solution.

The thus-collected crude enzyme solution (270 ml) had 1.05 unit/ml N-acetylglucosamine kinase activity. Specific activity per milligram of protein was 0.07 unit/mg. To the crude enzyme solution, 270 ml of 90% saturated ammonium sulfate solution was added, and after allowing to stand at a cold place for one hour, a supernatant was collected by centrifugation. To the collected supernatant, 135 ml of 90% saturated ammonium sulfate solution was added. The recovered precipitate was dissolved in 30 ml of PEN solution. This solution was dialyzed against PEN solution, to thereby obtain 43.5 ml of an enzyme preparation. This enzyme preparation exhibited 4.5 units/ml of N-acetylglucosamine kinase activity and specific activity was 0.21 unit/mg protein.

The N-acetylglucosamine kinase activity was determined according to the conventional method (Methods in Enzymology IX, p415–425,(1966)): i.e. 50 µl of 10 mM N-acetylglucosamine solution, 50 µl of 500 mM Tris-hydrochloric acid buffer (pH 7.8), 50 µl of 100 mM ATP solution, and 50 µl of 100 mM magnesium chloride were added to 50 µl of the enzyme preparation, which was maintained at 37° C. for 20–30 minutes for causing reaction As a control, water was used in place of ATP solution for the same test.

To stop the reaction, 500 µl of 5% zinc sulfate solution and 500 µl of 150 mM barium hydroxide solution were added to the above reaction mixture. After centrifugation for removal of precipitate, 166 µl of the supernatant was pipetted and 33 µl of a borate solution (4.95 g of boric acid was dissolved in 50 ml water and adjusted to pH 9.1 with 1N-potassium hydroxide, followed by dilution to 100 ml with water) was added thereto and the resultant solution was boiled for three minutes.

After boiling, the solution was cooled to room temperature, 1 ml of DMBA reagent (10 g of p-dimethylaminobenzaldehyde was dissolved in 100 ml of glacial acetic acid containing 12.5% 10N hydrochloric acid and was diluted tenfold, upon use, with glacial acetic acid) was added, and the solution was allowed to stand at 37° C. for 20 minutes. Absorption at 585 nm of the resultant solution was determined by spectrophotometer. By reference to a calibration curve, which had been prepared by use of N-acetylglucosamine of known concentration, residual N-acetylglucosamine in the reaction mixture was determined. Based on the data, the enzyme activity corresponding to consumption of 1 µmole N-acetylglucosamine per minute at 37° C. is defined as one unit (U).

Fractionation was performed with DEAE-Toyopearl 650M (2.2×25 cm column). Through elution with sodium chloride solution at a concentration gradient of 0–0.5 M, 47.5 ml of an active fraction was collected. To the fraction was added 95 ml of 90% saturated ammonium sulfate solution, the solution was allowed to stand at a cold place, and the precipitate was collected by centrifugation. The precipitate was dissolved in PEN (15 ml) and dialyzed against PEN, to yield 21 ml of partially purified enzyme exhibiting 6.84 units/ml of N-acetylglucosamine kinase activity. Specific activity per milligram of protein was 0.99 unit/mg.

(2) UDPAG synthesis

There was prepared a reaction mixture (10 ml) containing 200 mM phosphate buffer (pH 8.0), 20 mM magnesium chloride, 30 mM 5'-UMP, 20 mM N-acetylglucosamine, 100 mM glucose, and N-acetylglucosamine kinase preparation containing a predetermined activity (partially purified enzyme) derived from *Bacillus stearothermophilus* ATCC 15952. One gram of dry baker's yeast (Oriental Yeast Industries) was added thereto and incubated at 20° C. with stirring.

Figure 1:
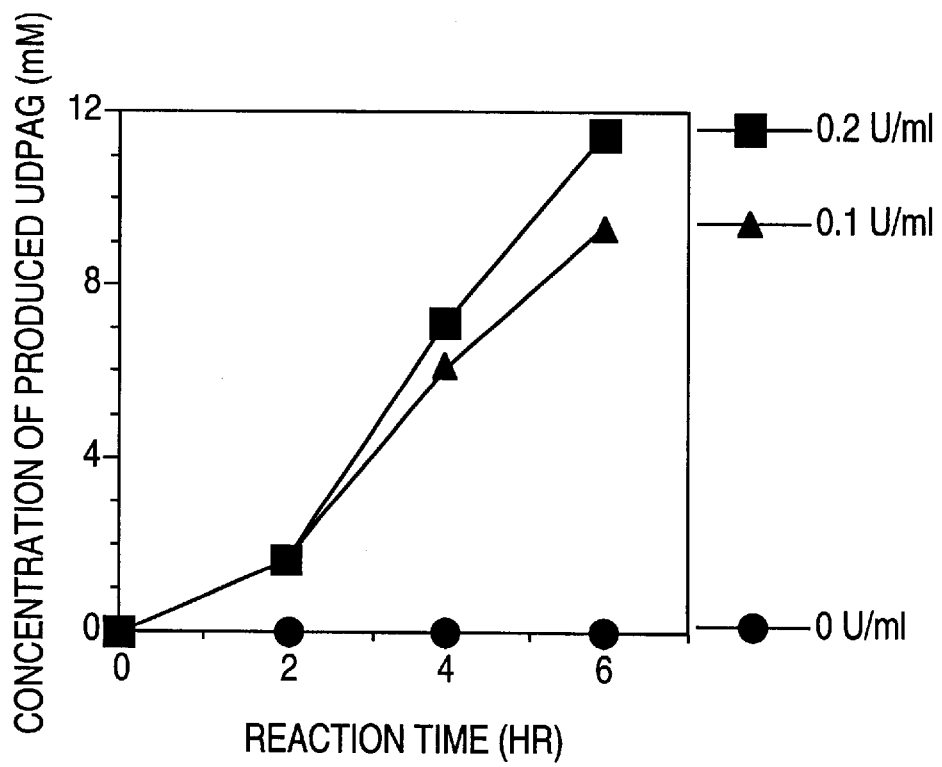
FIG. 1 is a graph showing chronological changes in the quantity of UDPAG produced in the co-presence of N-acetylglucosamine kinase derived from *Bacillus stearothermophilus* ATCC15952.

FIG. 1 shows chronological data obtained from the analysis of the reaction mixture. As is clearly evident from FIG. 1, UDPAG was not produced when N-acetylglucosamine kinase was not added. In contrast, when N-acetylglucosamine kinase was added at a concentration of 0.1 unit/ml, 9.2 mM UDPAG was produced; and when N-acetylglucosamine kinase was added at a concentration of 0.2 unit/ml, 11.5 mM UDPAG was produced in the reaction mixture during six hours from the start of reaction.

Example 2

A reaction mixture (10 ml) was prepared by mixing 200 mM phosphate buffer (pH 8.0), 20 mM magnesium chloride, 30 mM 5'-UMP, 20 mM N-acetylglucosamine, 100 mM glucose, and 2 units of N-acetylglucosamine kinase derived from *Escherichia coli* IAM1268 and prepared in a manner similar to that described in Example 1(1). To the resultant reaction mixture, 1 g of dry baker's yeast (Oriental Yeast Industries) was added to cause reaction at 20° C. with stirring.

Figure 2:
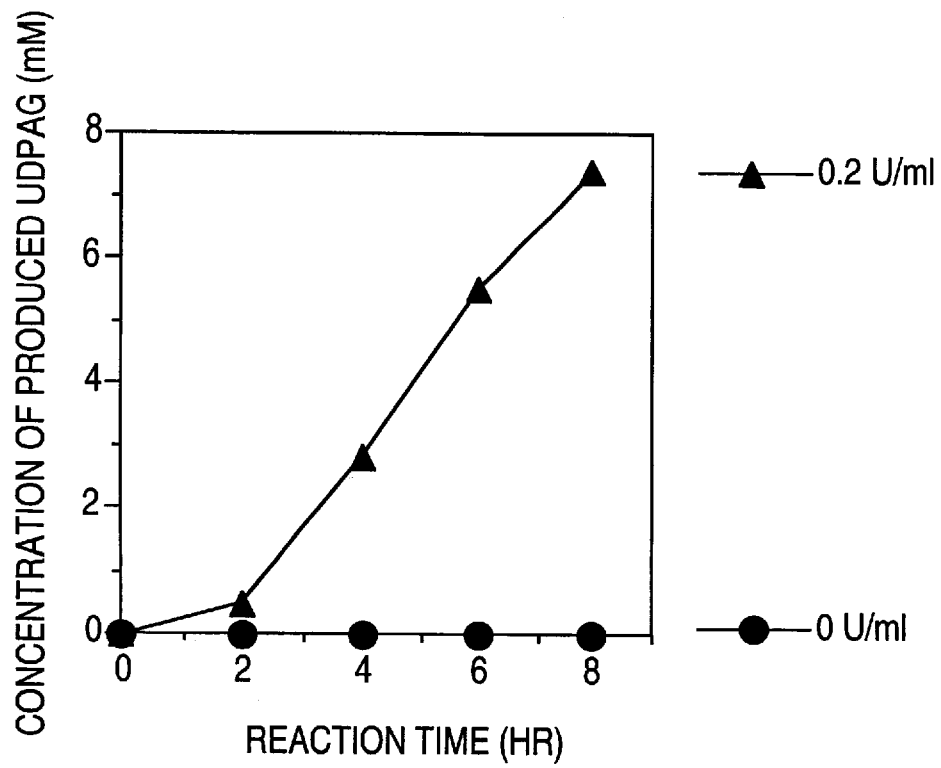
FIG. 2 is a graph showing chronological changes in the quantity of UDPAG produced in the co-presence of N-acetylglucosamine kinase derived from *Escherichia coli* IAM1268.

FIG. 2 shows the results of analysis of the reaction mixture. As is evident from FIG. 2, UDPAG was not produced at all when N-acetylglucosamine kinase was not added. In contrast, when N-acetylglucosamine kinase was added, 7.3 mM of UDPAG was produced during 8 hours from the start of reaction.

Example 3

Dry baker's yeast (1 g, Oriental Yeast Industries) was added to a reaction mixture (10 ml) containing 200 mM phosphate buffer (pH 8.0), 20 mM magnesium chloride, 30 mM 5'-UMP, 20 mM N-acetylglucosamine, 100 mM glucose, and 2 units of N-acetylglucosamine kinase derived from *Klebsiella planticola* IFO3317 and prepared in a manner similar to that described in Example 1(1), to thereby cause reaction at 20° C. with stirring.

Figure 3:
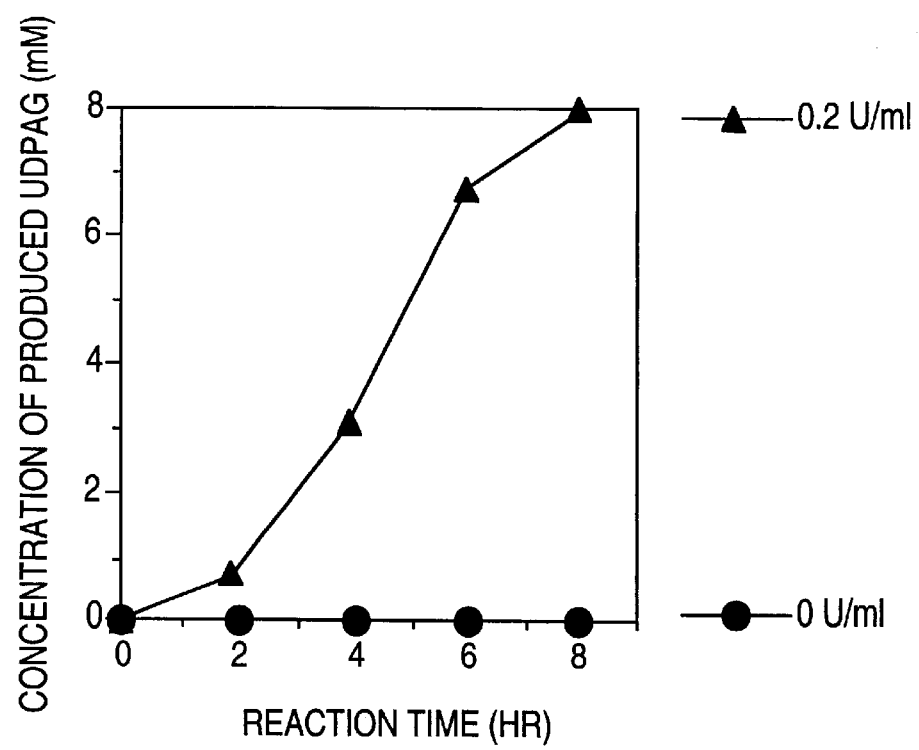
FIG. 3 is a graph showing chronological changes in the quantity of UDPAG produced in the co-presence of N-acetylglucosamine kinase derived from *Klebsiella planticola* IFO3317.

FIG. 3 shows the results of analysis of the reaction mixture. As is evident from FIG. 3, UDPAG was not produced when N-acetylglucosamine kinase was not added. In contrast, when N-acetylglucosamine kinase was added, 7.8 mM of UDPAG was produced during 8 hours from the start of reaction.

Example 4

Reaction was allowed to proceed for 24 hours in the reaction mixture (1,000 ml) of the same composition as used in Example 1. Subsequently, the pH of the reaction mixture was adjusted to 3.0 by addition of hydrochloric acid, and the supernatant was collected after centrifugation. The assayed quantity of UDPAG was 7.2 g.

Example 5

(1) Cloning of yqgR gene for coding N-acetylglucosamine kinase derived from *Bacillus subtilis*

Chromosomal DNA of M168 strain *Bacillus subtilis* (Tokyo Univ. Institute of Molecular Cell Biology, Molecular Genetics and Breeding Section) was prepared according to the method of Saito & Miura (Biochemica et Biophysica Acta., 72, 619 (1963)) by use of the obtained DNA as a template. The following two primer DNAs were synthesized by a conventional method, and *Bacillus subtilis* yqgR gene (submitted to EMBL/GENEBANK/DDBJ DATA BANKS, Accession No. D84432, Kobayashi et al) was amplified by PCR.

Primer (A): 5'-TATCTAGAACCACATGATTGAAAAGGAGCA-3'
Primer (B): 5'-TGAAGCTTCGCATTTrAACCTCCTATGCAG-3'

Amplification of the yqgR gene by PCR was performed by use of a DNA Thermal Cycler (Perkin-Elmer Cetus Instrument Co.) through twenty-five cycles of treatment, each cycle consisting of the steps of thermal denaturing (94° C., 1 minute), annealing (55° C. 1.5 minute), and polymerization (72° C., 3 minutes) of 100 $\mu$l reaction mixture which contained 50 mM potassium chloride, 10 mM Tris-hydrochloric acid (pH 8.3), 1.5 mM magnesium chloride, 0.001% gelatin, 0.2 mM DATP, 0.2 mM dGTP, 0.2 mM dCTP, 0.2 mM dTTP, template DNA: 0.1 $\mu$g, 0.2 $\mu$M primer DNA(A), 0.2 $\mu$M primer(B), and 2.5 units AmpliTaq DNA polymerase.

After amplification of the gene, the reaction mixture was treated with a mixture of phenol/chloroform (1:1), of which the aqueous fraction was mixed with twice the volume of ethanol for thereby precipitating DNA. The precipitated DNA was isolated by agarose gel electrophoresis performed according to the method as described (Molecular Cloning: same as aforementioned) and a 1.0 kb DNA was purified. The DNA was cleaved by restriction enzymes XbaI and Hind III, and ligated by use of T4 DNA ligase, with plasmid pTrc99A (Pharmacia Biotech Co.), which had also been cleaved by restriction enzymes XbaI and Hind III. The *Escherichia coli* K12 strain JM109 (Takara Shuzo Co.) was transformed with the ligation mixture. From the obtained ampicilline-resistant transformant, plasmid pTrcYQG-AB was isolated. The plasmid pTrcYQG-AB is a product obtained by inserting into pTrc99A, at the XbdaI-Hind III cleavage site downstream of the trc promoter, an XbaI-HindIII DNA fragment containing *Bacillus subtilis* yqgR gene and SD sequence.

(2) Preparation of a yqgR gene product derived from *Bacillus subtilis*

*Escherichia coli* JM109 harboring plasmid pTrcYQG-AB was inoculated in 100 ml 2×YT medium containing 100 $\mu$g/ml ampicillin and cultured at 37° C. with shaking. When the cell density reached 4×10$^8$ cells/ml, IPTG was added to achieve a final concentration of 1 mM and the cells were cultured for 5 more hours at 37° C. with shaking. After culturing, the cells were recovered by centrifugation (9,000× g, 10 minutes) and suspended into 20 ml buffer solution (50 mM Tris-hydrochloric acid (pH 7.5), 5 mM EDTA, 0.1% Triton X-100, 0.2 mg/ml lysozyme). After being maintained at 37° C. for one hour, the cells were lysed by ultrasonication. The cellular residue was removed by centrifugation (20,000×g, 10 minutes), The thus-obtained supernatant fraction was used as an enzyme sample, and N-acetylglucosamine kinase activity in the enzyme sample was measured by a method described in Example 1. The activity as determined and that of the reference cells (*Escherichia coli* JM109 harboring pTrc99A) are shown in the following table.

TABLE 1

| Strain/Plasmid | N-Acetylglucosamine kinase activity (Units/mg protein) |
|---|---|
| JM109/pTrc99A | 0.012 |
| JM109/pTrcYQG-AB | 0.571 |

(3) UDPAG synthesis

N-acetylglucosamine kinase solution having a predetermined enzyme activity and prepared in step (2) above and 0.5 g of dry baker's yeast (oriental Yeast Co.) were added to 5 ml solution containing 200 mM phosphate buffer solution (pH 8.0), 10 mM magnesium chloride, 50 mM 5'-UMP, 50 mM N-acetylglucosamine, and 200 mM glucose, and the resultant solution was maintained at 16° C. with stirring.

During reaction, a 0.2 ml aliquot of the solution was pipetted, boiled for 5 minutes, and centrifuged, and the obtained supernatant was diluted 250-fold and filtered through a 0.45 $\mu$m filter. The filtrate was submitted to HPLC analysis.

Figure 4:
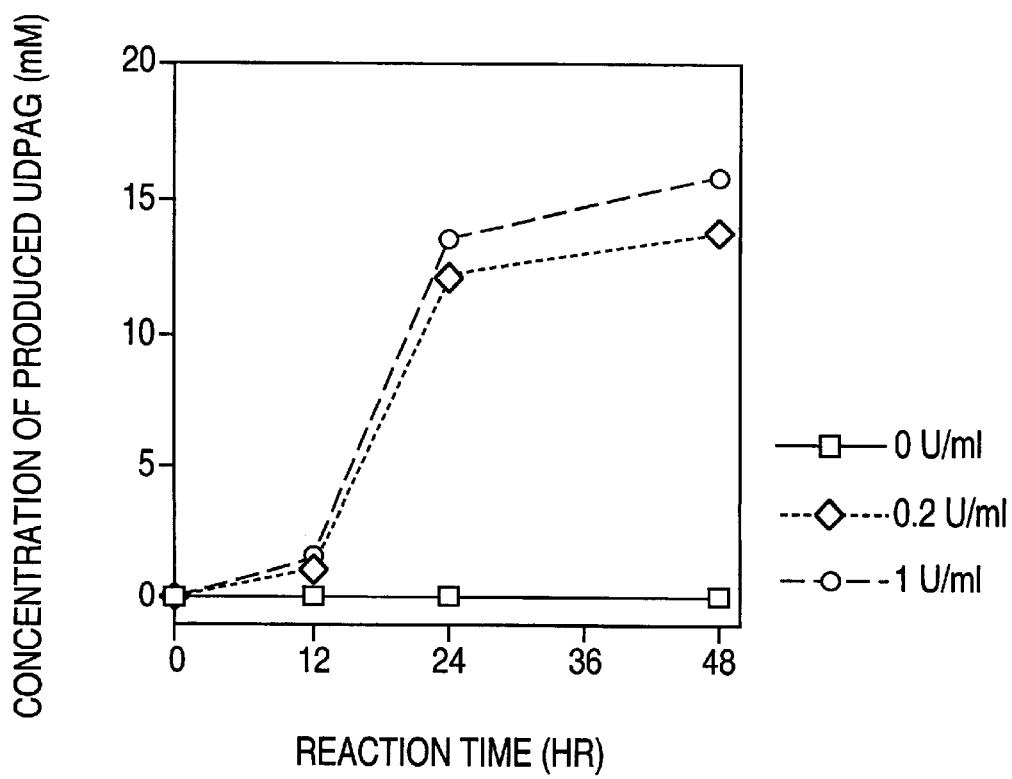
FIG. 4 is a graph showing chronological changes in the quantity of UDPAG produced in the co-presence of recombinant N-acetylglucosamine kinase derived from *Bacillus subtilis* M168.

FIG. 4 shows chronological data obtained from the analysis. As is evident from FIG. 4, UDPAG was not produced at all when N-acetylglucosamine kinase was not added. In contrast, when the enzyme was added at concentrations of 0.2 unit/ml and 1 unit/ml, 12.2 mM and 13.6 mM of UDPAG, respectively, were accumulated in 24 hours.

Example 6

(1) Cloning of N-acetylglucosamine phosphate mutase gene from yeast

Dry baker's yeast (Oriental Yeast Industries) was inoculated in the YPD medium. Orico Yeast was separated therefrom, and cultured in another YPD medium. From the medium, chromosomal DNA was prepared according to a conventional method. By use of the DNA as a template and also by use of the following two primer DNAS, a DNA fragment containing N-acetylglucosamine phosphate mutase (EC 5.4.2.3.) gene (agm1) (Eur. J. Biochem. 221, 741–747 (1994)) of yeast was prepared through PCR amplification:

Primer(C): 5'-TTGGCTGTTTGCTTGCTTGTGCGT-3'
Primer(D): 5'-CGATTGCAGAGCGAAACGACGAAA-3'

PCs amplification was effected by use of the same composition solution and reactor as used in Example 5, through 25 cycles of treatment; each cycle consisting of the steps of thermal denaturation (94° C., 1 minute), annealing (37° C., 2 minutes), and polymerization (72° C., 3 minutes).

After amplification of the gene, a 2.2 kb DNA fragment was obtained through a purification step similar to that employed in Example 1. By use of the DNA as a template and the following two primer DNAS, the DNA fragment containing N-acetylglucosamine phosphate mutase gene (agm1) derived from yeast was amplified again by PCR. The conditions of the second PCR experiment were the same as those employed in the first experiment.

Primer (E): 5'-AAGGTTGATTACGAGCAATTGTGC-3'
Primer (F): 5'-TCAAGCAGATGCCTTAACGTGCTC-3'

After amplification of the gene, a 1.7 kb DNA fragment was purified in a manner similar to that described above. The recovered DNA was blunt-ended by use of a DNA blunting kit (Takara Shuzo Co.). After this DNA was digested with restriction enzyme Ncov, the DNA was ligated with blunt-ended plasmid pTrc99A (Pharmacia Biotech Co.) by use of T4 DNA ligase. The *Escherichia coli* K12 strain JM109 was transformed with the reaction mixture. From the obtained ampicillin resistant transformant, plasmid pTrc-agm1 was isolated. The plasmid pTrc-agm1 is a product obtained by inserting, into pTrc99A at NcoI cleavage site downstream of the trc promoter, yeast agm1 gene so as to match the starting codon ATG of yeast agm1 gene to the ATG at the NcoI cleavage site. The obtained transformant was named JM109 [pTrc-agm1].

(2) Preparation of N-acetylglucosamine phosphate mutase derived from yeast

JM109[pTrc-agm1] was cultured overnight in 25 ml of 2×YT medium containing 100 μg/ml ampicillin at 37° C., and the cultured cells were inoculated into 500 ml of 2×YT medium containing 100 μg/ml ampicillin. After culturing at 37° C. for 2 hours, IPTG was added at a final concentration of 1 mM and the cell culture was maintained at 37° C. for 5 hours, then at 20° C. overnight. Subsequently, the cells were recovered by centrifugation (9,000×g, 20 minutes). The recovered cells were suspended in 50 mM imidazol buffer solution (pH 6.8). The cells were lysed (50 W, 3 times, 5 minutes each time) by an ultrasinic destruction machine (Model 450 sonifer: Branson Co.), and a soluble fraction (the supernatant) was recovered by centrifugation at 15,000 rpm for 30 minutes.

The thus-obtained supernatant was used as an enzyme sample, and was submitted to N-acetylglucosamine phosphate mutase activity assay. The activity is shown in Table 2, along with that of the reference microorganism (*Escherichia coli* JM109 harboring pTrc99A).

N-acetylglucosamine phosphate mutase activity was determined by measuring the activity of transforming N-acetylglucosamine 1-phosphate to N-acetylglucosamine 6-phosphate, according to the method described in published literature (European Journal of Biochemistry, No. 221, 741 (1994)).

Briefly, a N-acetylglucosamine phosphate mutase sample was added to a mixture of 50 mM imidazol (pH 6.8), 100 mM potassium chloride, 10 mM magnesium chloride, 0.1 mM EDTA, 20 μM glucose 1,6-bisphosphate, and 2 mM N-acetylglucosamine 1-phosphate, the mixture being maintained at 30° C. Also, as a control, water was used in place of glucose 1,6-bisphosphate.

An equivalent volume of 1M sulfuric acid solution was added to and mixed with the above-described solution to inactivate the enzyme. After boiling for 10 minutes, the solution was cooled to 25° C. Thus, heat-fragile N-acetylglucosamine 1-phosphate was decomposed to release inorganic phosphoric acid. The released inorganic phosphoric acid was determined by the following method. After the sample (200 μl) was cooled to 25° C., 700 μl distilled water, 100 μl amidol reagent (100 g sodium hyposulfite and 5 g amidol dissolved in 500 ml water), and 70 μl of 8.3% ammonium molybdate (41.5 g of ammonium molybdate dissolved in 500 ml water with ammonium hydroxide) were added thereto and the resultant solution was maintained at room temperature for 10 minutes. Absorbency at 750 nm was determined by use of a spectrometer. Based on a calibration curve of absorbency 0.3867 for 1 mM inorganic phosphoric acid, inorganic phosphoric acid was quantified, and consumption of N-acetylglucosamine 1-phosphate by enzyme reaction was estimated. The activity corresponding to conversion of 1 μmole N-acetylglucosamine 1-phosphate to N-acetylglucosamine 6-phosphate per minute at 30° C. is defined as one unit.

TABLE 2

| Strain/Plasmid | N-acetylglucosamine phosphate mutase activity (Units/mg protein) |
|---|---|
| JM109/pTrc99A | 0.01 or lower |
| JM109/pTrc-agml | 5.70 |

The UDPAG synthesis described hereinlater makes use of the transforming activity of N-acetylglucosamine phosphate mutase in conversion of N-acetylglucosamine 6-phosphate to N-acetylglucosamine 1-phosphate. Therefore, the transforming activity was estimated by quantifying the formed N-acetylglucosamine 1-phosphate when N-acetyglucosamine 1-phosphate In the reaction mixture was replaced by N-acetylglucosamine 6-phosphate. The specific activity for converting N-acetylglucosamine 6-phosphate to N-acetylglucosamine 1-phosphate was found to be only 1/30 that for the reverse reaction, i.e., the reaction from N-acetylglucosamine 1-phosphate to N-acetylglucosamine 6-phosphate.

(3) Cloning of UDPAG pyrophosphorylase gene from *Escherichia coli*

UDPAG pyrophosphorylase of *Escherichia coli* is known to be identical with glucosamine uridyl transferase (EC2.7.23) (glmU) (Journal of Bacteriology, 175, 19, 6150 (1993)). Therefore, the chromosomal DNA of *Escherichia coli* IFO3972 was prepared according to the method of Saito & Miura (Biochemica et Biophysica Acta,72, 619 (1993)), and by use of the DNA as a template, a DNA fragment containing UDPAC pyrophosphorylase gene (Biochem. J. 224, 799–815 (1984)) was amplified by PCR with the following two primer DNAs:

Primer (G): 5'-CCTGCTGATATAAAACCCCCCTGT-3'
Primer (H): 5'-CCCGAAGCTTGTAGAGAGTGGGGT-3'

PCR amplification was performed by use of the same composition solution and same reactor as those employed in Example 5, through 25 cycles of the treatment, each cycle consisting of the steps of thermal denaturing (94° C., 1 minute), annealing (55° C., 2 minutes), and polymerization (72° C., 3 minutes).

After amplification of the gene, a 1.5 kb DNA fragment was purified in a manner similar to that described in Example 5. The recovered DNA was blunt-ended by use of a DNA blunting kit (Takara Shuzo Co.). After the DNA was digested with restriction enzyme DraI, the DNA was ligated by use of T4 DNA ligase with plasmid pUC18 that had been digested with restriction enzyme SmaI, The plasmid was digested with restriction enzyme EcoRI and HindIII. In the same manner as described above, a 1.5 kb DNA fragment was purified. Subsequently, the DNA was ligated, by use of T4 DNA ligase, with plasmid, pTrc99A (Pharmacia Biotech Co.) which had been digested with restriction nuclease EcoRI and HindIII. The *Escherichia coli* K12 strain JM109 was transformed by use of the reaction mixture, and from the obtained ampicillin-resistant transformant, plasmid pTrc-glmU was isolated. The pTrc-glmU is a product obtained by inserting into pTrc99A, at the SmaI-HindIII recognition site downstream of the trc promoter, *Escherichia coli* glmU gene. The obtained transformant was named JM109[pTrc-glmU].

(4) Preparation of UDPAG pyrophosphorylase

JM109[pTrc-glmU] was cultured overnight at 37° C. in 25 ml 2×YT medium containing 100 μg/ml ampicillin. The culture was inoculated into 500 ml 2×YT medium containing 100 μg/ml ampicillin, and incubated at 37° C. for 2 hours. IPTG was added thereto to achieve a final concentration of 1 mM, and the cells were continuously cultured overnight. After culturing, the cells were recovered by centrifugation (4° C., 9,000×g, 20 minutes). The recovered cells were suspended in 50 mM Tris-hydrochloric acid solution (pH 7.5) and lysed (50 W, 3 times, 5 minutes each time) by a ultrasonic destruction machine (Model 450 sonifer: Bronson Co.). After centrifugation (4° C., 15,000 rpm, 30 minutes), the soluble fraction (supernatant) was recovered.

The obtained supernatant, serving as enzyme sample, was subjected to UDPAG pyrophosphorylase activity assay. Table 3 shows the assay result, along with that of the reference cells (Escherichia JM109 harboring pTrc99A).

TABLE 3

| Strain/Plasmid | UDPAG pyrophosphorylase activity (Units/mg protein) |
| --- | --- |
| JM109/pTrc99A | 0.29 |
| JM109/pTrc-glmU | 16.52 |

The UDPAG pyrophosphorylase activity was estimated in the following manner, by determining the decomposing activity from UDPAG and pyrophosphoric acid to N-acetylglucosamine 1-phosphate and UTP.

Briefly, to a mixture of 50 mM Tris-hydrochloric acid buffer (pH 7.5), 5 mM magnesium chloride, 3 mM sodium pyrophosphate, and 1 mM UDPAG, a UDPAG pyrophosphorylase enzyme sample was added in an amount that corresponded to about 6 $\mu$g/ml reaction mixture. Subsequently, the mixture was allowed to react for 5 minutes at 37° C. In a control, sodium pyrophosphate solution was replaced with water, and the similar reaction was performed.

The reaction was stopped by boiling for 5 minutes, and the solution was diluted 30-fold and submitted to HPLC analysis. For the analysis, ODS-AQ312 column (YMC Co.) and 0.5M potassium dihydrogenphosphate solution were used for elution. From the analysis data, residual quantity of UDPAG was determined and the activity corresponding to decomposition of 1 $\mu$mole UDPAG per minute at 37° C. is defined as one unit.

(5) Synthesis of UDPAG with recombinant enzymes

The prepared recombinant enzymes (N-acetylglucosamine kinase: 0.2 unit, N-acetylglucosamine phosphate mutase: 0.5 unit, UDPAG pyrophosphorylase: 5 unit) were added to 5 ml solution containing 200 mM glucose, 50 mM N-acetylglucosamine, 50 mM UMP, 200 mM potassium dihydrogenphosphate (pH 8.0), 10 mM magnesium chloride, and 5% (w/v) dry baker's yeast (Oriental Yeast Co.), and the resultant mixture was stirred at 300 rpm (20° C.). Fifty percent glucose solution (volume: 1/14 that of the reaction mixture) was added at 16, 24, 40, 48, 64 and 72 hours following the start of the reaction.

Figure 5:
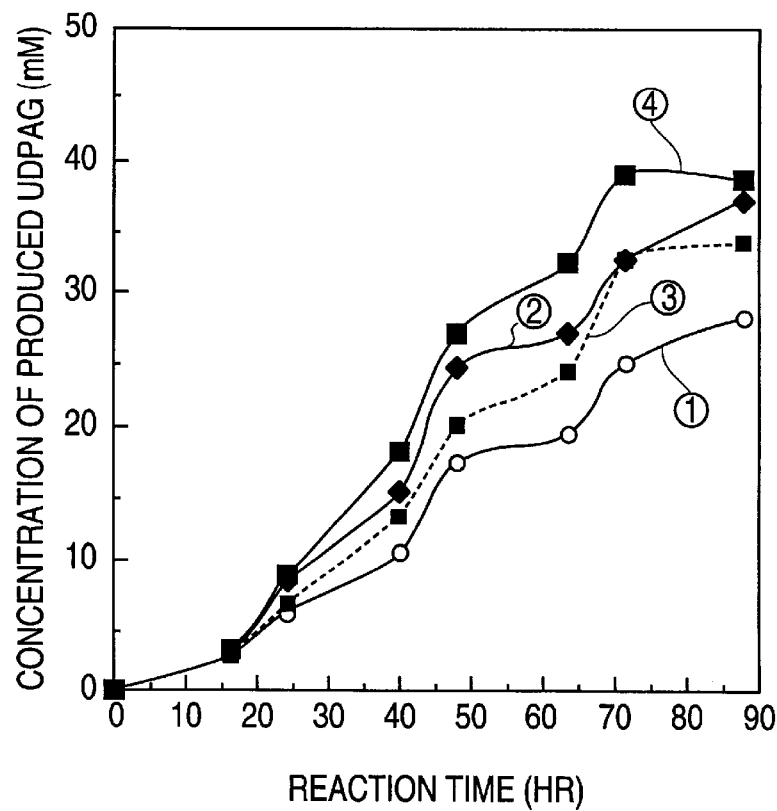
FIG. 5 is a graph showing chronological changes in the quantity of UDPAG produced in the co-presence of a combination of recombinant N-acetylglucosamine kinase derived from *Bacillus subtilis* M168, recombinant N-acetylglucosamine phosphate mutase derived from baker's yeast, and/or recombinant UDPAG pyrophosphorylase derived from *Escherichia coli* E102.

FIG. 5 shows chronological data of the analysis. When glucose was added, the combination of 5% yeast and N-acetylglucosamine kinase yielded 27 mM UDPAG after 88 hours. As shown in FIG. 5, in the following three cases; i.e., when UDPAG pyrophosphorylase was combined with N-acetylglucosamine kinase, N-acetylglucosamine phosphate mutase was combined therewith, and both UDPAG pyrophosphorylase and N-acetylglucosamine phosphate mutase were combined therewith, the accumulated quantity of UDPAG increased to 33 mM, 37 mM, and 39 mM, respectively.

Example 7

Example 6 is directed to a small test tube experiment; however, in Example 7, a scale-up test was performed in a jar fermenter. The recombinant DNA enzyme mixture (N-acetylglucosamine kinase: 120 units, N-acetylglucosamine phosphate mutase: 750 units, UDPAG pyrophosphorylase: 750 units) prepared in Example 5(2) and Example 6(2) and (4) was added to a 1.5-liter solution containing 400 mM glucose, 100 mM N-acetylglucosamine, 100 mM UMP, 200 mM potassium phosphate (pH 8.0). 20 mM magnesium chloride, and 5%(w/v) dry baker's yeast (Oriental Yeast Co). and the resultant solution was stirred at 700 rpm at 23° C. under aeration at 1.5 liter/minute. During the reaction, an antifoaming agent, "ainol" was added. Also, 54 g glucose was added at 12, 20, and 36 hours following the start of reaction.

FIG. 6 shows the results of analysis. After 45 hours of reaction, accumulation of UDPAG was found to be 82 mM.

Example 8

Up to Example 7, an explanation was given of the case in which UDPAG synthesis was performed through use of dry baker's yeast. In Example 8 is described that UDPAG may be synthesized ln vitro, in place of using dry baker's yeast; for example, by use of an "UTP-generating system" comprising UMP kinase, polyphosphate kinase, and adenylate kinase. For synthesis of UTP from UDP, nucleoside diphosphate kinase is required; however, adenylate kinase also exhibits the same activity, so that the requirement to use nucleoside diphosphate kinase may be omitted.

(1) Cloning of UMP kinase gene from Escherichia coli

Chromosomal DNA of *Escherichia coli* K12 strain JM109 (Takara Shuzo Co.) was prepared according to the method of Saito & Miura (Biochemica et Biophysica Acta, 72, 619 (1963)). By use of the above DNA as a template, the following two primer DNAs were synthesized in a conventional manner, and Escherichia coil UMP kinase (pyrH) gene (Genetics (Life Sci. Adv.), 11, 59–65 (1992)) was amplified by PCR.

Primer (I): 5'-TTCCATGGCTACCAATGCAAAAC-3'
Primer (J): 5'-TTGGATCCTTATTCCGTGATTAAAGTCCC-3'

PCR amplification of pyrH gene was performed by use of the same composition solution and same reactor as those used in Example 5, through 25 cycles of the treatments, each cycle consisting of the steps of thermal denaturing (94° C., 1 minute), annealing (55° C., 2 minutes), and polymerization (72° C., 4 minutes).

After amplification of the gene, a 0.74 kb DNA fragment was purified in a menner similar to that described in Example 5. The DNA was cleaved with the restriction enzymes NcoI and BamHI, and was ligated by T4 DNA ligase with plasmid pTrc99A (Pharmacia Biotech Co.) that had been digested with restriction enzymes NcoI and BamHI. With the reaction mixture, *Escherichia coli* JM109 was transformed, and from the obtained ampicillin resistant transformant, plasmid pTP01 was isolated. The plasmid pTP01 is a product obtained by inserting into pTrc99A, at the NcoI-BamHI cleavage site downstream of the trc promoter and Shine-Dargano sequence, a NcoI-BamHI DNA fragment containing *Escherichia coli* pyrH gene.

(2) Preparation of UMP kinase derived from *Escherichia coli*

*Escherichia coli* JM109 harboring plasmid pTP01 was inoculated in 10 ml LB medium containing 50 $\mu$g/ml ampicillin, and shaken at 30° C. When the cell density reached 4×10$^8$ cells/ml, IPTG was added at a final concentration of 1 mM, and was cultured with shaking for additional 5 hours at 30° C.

After culturing, the cells were recovered by centrifugation (9,000×g, 10 minutes) and suspended in 2 ml buffer solution (50 mM Tris-hydrochloric acid (pH 7.5). 50 mM potassium chloride, 2 mM magnesium chloride). The suspension was submitted to ultrasonic treatment, and by separating the supernatant through centrifugation (20,000×g, 10 minutes), a precipitate was obtained as an enzyme sample.

UMP kinase activity of this enzyme sample is compared with that of reference microorganism (*Escherichia coli* carrying pTrc99A) in Table 4.

The activity of UMP kinase in the present invention was estimated in terms of a unit defined and determined by the following method. The sample was incubated in 50 mM Tris-hydrochloric acid (pH 7.5), 50 mM potassium chloride, 2 mM magnesium chloride, 3 mM UTP and 3 mM ATP at 30° C., and boiled for one minute to inactivate the enzyme. UDP was quantified with HPLC, and the activity corresponding to generation of 1 μmole UDF per minute at 30° C. is defined as one unit.

TABLE 4

| Bacteria/Plasmid | UMP kinase activity (Units/mg protein) |
|---|---|
| JM109/pTrc99A | 0.1 or lower |
| JM109/pTPol | 4.9 |

(3) Cloning of polyphosphate kinase gene from *Escherichia coli*

Chromosomal DNA of *Escherichia coli* K12 strain JM 109 (Takara Shuzo Co.) was prepared according to the method of Saito & Miura (Biochemica et Biophysica Acta, 72, 619 (1963)). By use of the DNA as a template, the following two primer DNAs were synthesized according to a conventional method, and *Escherichia coli* polyphosphate kinase (ppk) gene (J. Biol. Chem., 267, 22556–22561 (1992)) was amplified by PCR.

Primer (K): 5'-TACCATGGGTCAGGAAAAGCTATA-3'
Primer (L): 5'-ATGGATCCTTATTCAGGTTGTTCGAGTGA-3'

PCR amplification of the ppk gene was performed by use of the same composition solution and the same reactor as described in Example 5, through 25 cycles of treatment, each cycle consisting of the steps of thermal denaturing (94° C., 1 minute), annealing (55° C., 1.5 minutes), and polymerization (72° C., 1.5 minutes). After amplification of the gene, a 1.0 kb DNA fragment was purified. The DNA was cleaved by restriction enzymes NcoI and BamHI, and ligated by use of T4 DNA ligase with plasmid pTrc99A (Pharmacia Biotech Co.) that had been digested with restriction enzymes NcoI and BamHI. The *Escherichia coli* JM109 was transformed with reaction mixture, and from the ampicillin resistant transformant, plasmid pTrc-PPK was isolated, The plasmid pTrc-PPK is a product obtained by inserting into pTrc99A, at the NcoI-BamHI cleavage site downstream of the trc promoter, an NcoI-BamHI DNA fragment containing *Escherichia coli* ppk gene.

(4) Preparation of polyphosphate kinase derived from *Escherichia coli*

*Escherichia coli* JM109 carrying plasmid pTrc-PPK was inoculated in 2×YT medium (300 ml) containing 100 μg/ml ampicillin, and shaken at 37° C. When the density of the cells reached 4×10$^8$ cells/ml, IPTG was added to make a final concentration of 1 mM, and cultured for 5 hours with shaking at 30° C.

After culturing, the cells were recovered by centrifugation (9,000×g, 10 minutes), and suspended in 60 ml buffer solution (50 MM Tris-hydrochloric acid (pH 7.5), 5 mM EDTA, 0.1% Triton X-100, 0.2 mg/ml lysozyme) for 1 hour at 37° C. The calls were subjected to ultrasonic treatment, and lysed cell debris was separated by centrifugation (20, 000×g, 10 minutes). The supernatant was dialyzed against 50 mM Tris-hydrochloric acid buffer (pH 7.8) containing 5 mM magnesium chloride and 1 mM 2-mercaptoethanol, to thereby obtain a crude enzyme solution.

The polyphosphate kinase activity of the crude enzyme preparation was assayed In comparison with that of *Escherichia coli* JM109 carrying pTrc99A, and the results are shown in Table 5.

TABLE 5

| Strain/Plasmid | Polyphosphate kinase activity (Units/mg protein |
|---|---|
| JM109/pTrc99A | 0.00018 |
| JM109/pTrc-PPK | 0.19 |

The activity unit of polyphosphate kinase was estimated in the following way. The enzyme sample was added to 5 mM Tris-hydrochloric acid buffer solution (pH 7.8) containing 5 mM magnesium chloride, 100 mM ammonium sulfate, 5 mM ADP, polyphosphate (150 mM as inorganic phosphoric acid), and incubated at 37° C. until being boiled for one minute to inactivate the enzyme. The unit of activity was determined by HPLC, and the activity corresponding to generation of 1 μmole ATP per minute at 37° C. is defined as one unit.

The crude enzyme solution was fractionated through DEAE Toyopearl 650M (Toso Co.) column chromatography with an elution solution of concentration gradient 0–0.5M NaCl, and polyphosphate kinase fraction was obtained as a polyphosphate kinase enzyme sample. The specific activity of polyphosphate kinase in the thus-prepared sample was 0.6 unit/mg protein.

(5) Cloning of adenylate kinase derived from *Escherichia coli*

Chromosomal gene of *Escherichia coli* K12 strain JM109 (Takara Shuzo Co) was prepared according to the method of Saito & Miura (Biochem. Biopys. Acta 72, 619(1963)), By use of the above DNA as a template, the following two primer DNAs were synthesized in a conventional manner, and *Escherichia coli* adenylate kinase (adk) gene (Nucleic Acids Res., 13(19), 7139–7151 (1985)) was amplified by PCR.

Primer (M): 5'-ATGGATCCCGTTTCAGCCCCAGGTGCC-3'
Primer (N): 5'-ATAAGCTTGGCCTGAGATTGCTGATAAG-3'

PCR amplification of adk gene was performed by use of the same compositions of reaction mixture and the same reactor as employed In Example 5; through 25 cycles of treatment, each cycle consisting of the steps of thermal denaturing (94° C., 1 minute), annealing (56° C., 1 minute), and polymerization (72° C., 3 minutes).

After amplification of the gene, in a manner similar to that described in Example 5, a 1.0 kb DNA fragment was purified. The DNA fragment was cleaved with restriction enzymes BamHI and HindIII, and was ligated, by T4 DNA ligase, with plasmid pUC18 (Takaara Shuzo Co.) that had been digested with restriction enzymes BamHI and HindIII. *Escherichia coli* JM109 was transformed with the reaction mixture, and the ampicillin resistant transformant was obtained. From the transformed cells, PUC-ADK was isolated. The plasmid pUC-ADK is a product obtained by inserting into pUC18, at the BamHI-HindIII cleavage sites downstream of the lac promoter, BamHI-HindIII DNA fragment containing the *Escherichia coli* adk gene.

(6) Preparation of adenylate kinase derived from *Escherichia coli*

*Escherichia coli* JM109 carrying plasmid pUC-ADK was Inoculated into 300 ml 2×YT medium containing 100 μg/ml ampicillin, and cultured at 37° C. with shaking. When the cell density reached 4×10⁸ cells/ml, IPTG was added to attain a final concentration of 1 mM, and cells were cultured for an additional 5 hours at 30° C.

After culturing, the cells were recovered by centrifugation (9,000×g, 10 minutes), suspended In 60 ml buffer solution containing 50 mM Tris-hydrochloric acid (pH 7.5), 5 mM EDTA, 0.1% Triton X-100, 0.2 mg/ml lysozyme), and maintained for one hour at 37° C. Subsequently, the cells were lysed by ultrasonication, and through centrifugation (20,000×g, 10 minutes), the cell debris was separated and removed. The supernatant was dialyzed against 50 mM Tris-hydrochloric acid (pH 7.8) containing 5 mM magnesium chloride and 1 mM 2-mercaptoethanol, and a crude enzyme solution was obtained. Table 6 shows the adenylate kinase activity of the crude enzyme assayed, along with that of reference cells (*Escherichia coli* JM109 carrying pUC18).

TABLE 6

| Strain/Plasmid | Adenylate kinase activity (units/mg protein |
|---|---|
| JM109/pUC18 | 1.9 |
| JM109/pUC-ADK | 134 |

The unit of the adenylate kinase activity was estimated in the following way.

The enzyme sample was added to 50 mM Tris-hydrochloric acid buffer solution (pH 7.8) containing 5 mM magnesium chloride, 5 mM ATP, and 5 mM AMP, and was incubated at 37° C. for reaction. The enzyme was deactivated by boiling for one minute. ADP in the reaction mixture was quantified by HPLC and the activity corresponding to that capable of generating 2 μmole ADP per minute at 37° C. is defined as one unit.

The crude enzyme was fractionated through DEAE Toyopearl 650M (Toso Co.) column chromatography with an elution solution (sodium chloride) of concentration gradient 0–0.5 M. The adenylate kinase active fraction was collected, and used as an adenylate kinase enzyme sample. The specific activity of polyphosphate kinase in this enzyme sample was assayed and found to be 344 units/mg protein.

(7) Synthesis of UDPAG with a UTP-generating system comprising UMP kinase, polyphosphate kinase, and adnylate kinase An enzyme sample containing 0.1 unit/ml polyphosphate kinase, 2.5 unit/ml adenylate kinase, 0.5 unit/ml N-acetylglucosamine kinase, 0.5 unit/ml UMP kinase, 0.05 unit/ml N-acetylglucosamine phosphate mutase, and 1.0 unit/ml UDPAG pyrophosphorylase was added to 200 mM Tris-hydrochloric acid buffer solution (pH 7.8) containing 10 mM magnesium chloride, 100 mM ammonium sulfate, polyphosphate (75 mM as inorganic phosphoric acid), 10 mM UMP, and 3 mM AMP, and incubated at 37° C. for 24 hours. 3.4 mM UDPAG was found to be produced.

INDUSTRIAL APPLICABILITY

The present invention enables efficient production of UDPAG even from N-acetylglucosamine as a substrate, which previously had been evaluated as being of very limited use.

What is claimed is:

1. A process for preparing uridine diphosphate-N-acetylglucosamine (UDPAG) from uridilic acid (UMP) and N-acetylglucosamine by use of microorganism cells, comprising adding N-acetylglucosamine kinase to the reaction mixture.

2. The process according to claim 1, wherein the microorganism cell is a yeast cell.

3. The process according to claim 1, wherein N-acetylglucosamine kinase is derived from bacteria.

4. The process according to claim 1, wherein N-acetylglucosamine phosphate mutase and/or uridine diphosphate-N-acetylglucosamine pyrophosphorylase are added thereto.

5. A process for preparing UDPAG from uridine triphosphate (UTP) and N-acetylglucosamine by use of an enzyme, which process comprises adding a combination of N-acetylglucosamine kinase, N-acetylglucosamine phosphate mutase, and uridine diphosphate-N-acetylglucosamine pyrophosphorylase as enzymes.

6. The process according to claim 5, wherein a UTP-generating system is added in place of UTP.

7. The process according to claim 6, wherein the UTP-generating system is a system using microorganism cells.

8. The process according to claim 6, wherein the UTP-generating system is a system using an enzyme.

9. The process according to claim 6, wherein the UTP-generating system is a coupling system comprising a UTP-generating system and an adenosine triphosphate (ATP)-generating system.

10. The process according to claim 9, wherein the UTP-generating system is a system of generating UTP by addition of uridylate kinase to UMP, and simultaneously regenerating ATP by addition of polyphosphate kinase, adenylate kinase, and polyphosphate to adenylic acid (AMP).

* * * * *